United States Patent [19]

Bancroft et al.

[11] Patent Number: 4,611,120

[45] Date of Patent: Sep. 9, 1986

[54] SUPPRESSION OF MOLECULAR IONS IN SECONDARY ION MASS SPECTRA

[76] Inventors: G. Michael Bancroft, 62 Heathcote Avenue, London, Ontario, Canada, N6G 1V5; William J. Chauvin, 10 Sandalwood Crescent, London, Ontario, Canada, N6G 2Z7; Norman S. McIntyre, 94 Shavian Boulevard, London, Ontario, Canada, N6G 2P3; James B. Metson, 310 Oxford Street East, London, Ontario, Canada, N6A 1V5

[21] Appl. No.: 648,727

[22] Filed: Sep. 7, 1984

[30] Foreign Application Priority Data

Oct. 28, 1983 [CA] Canada .................................. 439946

[51] Int. Cl.$^4$ ............................................ G01N 23/00
[52] U.S. Cl. ...................... 250/307; 250/309; 250/440.1
[58] Field of Search .................. 250/305, 309, 396 R, 250/440.1, 492.2, 307

[56] References Cited

U.S. PATENT DOCUMENTS 3,819,941 6/1974 Carrico ........................... 250/396 R
4,255,661 3/1981 Liebl .............................. 250/396 R Primary Examiner—Bruce C. Anderson
Attorney, Agent, or Firm—John P. White

[57] ABSTRACT

A method of suppressing molecular ions in the secondary ion mass spectra of conducting, semiconducting and insulating specimens is described using a commercial secondary ion microscope/mass analyzer with unconventional primary beam conditions and uncoated samples, so as to almost eliminate the contribution of molecular ions to the mass spectrum. This results in excellent discrimination for major and trace element detection in these materials, including for example complete resolution of the rare earth elements in a number of minerals. Complete elemental analysis for a much enhanced range of elements down to the ppb level is now possible. The method also facilitates the analysis of insulating materials which would undergo surface charging distortion under any other condition.

14 Claims, 15 Drawing Figures

SUPPRESSION OF MOLECULAR IONS IN SECONDARY ION MASS SPECTRA

This invention relates to a method of suppressing molecular ions in the secondary ion mass spectra conducting, semiconducting and insulating specimens and the removal of charge distortions from the spectra of insulating materials. A specimen is mounted uncoated in a specimen holder such that it is isolated electrically and offset behind the stage of a secondary ion microscope mass analyzer. A mask is then secured above the specimen and is attached electrically to the stage. A high energy primary ion beam is impinged on said specimen so as to produce secondary ions and further the specimen is charged such that a potential difference in excess of 300 V exists between the surface of the specimen and the mask secured above. The secondary ions are focussed through an immersion lens into an analyser so as to allow for the recording of the secondary ion mass spectra of the specimen.

A preferred embodiment of this invention is the high energy primary ion beam which may be a negatively charged ion beam comprised of $O^-$ ions or a positively charged ion beam comprised of one of $O_2^+$, $Ar^+$ or $Cs^+$.

While $O^-$ primary ions are more generally applicable, the use of a $Cs^+$ ion beam is definitely preferred for specific analyses such as measurement of oxygen where $O^+$ ions are obviously not useful.

BACKGROUND OF THE INVENTION

The potential of Secondary Ion Mass Spectrometry (SIMS) in the analysis of solid samples such as minerals has long been recognized, and the geochemical applications have been discussed by J. F. Lovering in *NBS Spec. Publ.* 427, 135–178 (1975) and N. Shimuzu and S. R. Hart in *Ann. Rev. Earth Planet Sci.* 10, 483–526 (1982). The ability to cover virtually the complete periodic table, coupled with excellent sensitivity for many elements and high spatial resolutions, should give the technique wide application in the characterization and elemental analysis of complex solids such as minerals. The high signal/background ratios inherent in mass spectrometry coupled with excellent ion yields make it possible to attain detection limits of parts per billion for a number of elements, as set out by S. J. B. Reed in *Scanning* 3, 119–127 (1980).

As shown in FIG. 1, in this method a high energy "primary" ion beam such as $^{16}O^-$ impinges on the sample of interest, and atoms and ions are ejected from the sample. Normally positive ions from the sample (at 4500 V in the CAMECA instrument) are accelerated towards an immersion lens, and the ions are then mass analyzed. A typical mass spectrum of a gold coated sphene is shown in FIG. 2. This spectrum indicates that almost all the elements in the periodic table can be analyzed, and that the intensities (and thus sensitivities) are excellent. Also the spatial resolution is high, down to 5 microns in this instrument. However, minor and trace elements cannot be easily detected because of molecular ions which have the same nominal mass as atomic species. Thus, for example, $^{40}Ca^{16}O^+$ overlaps with $^{56}Fe^+$, and the oxides of the light rare earth elements overlap with the atomic ions of the heavy rare earths.

Thus the potential of SIMS has yet to be realized, perhaps with the exception of lead isotope determinations which have been used with success in dating lunar and terrestrial samples, as disclosed by C. A. Anderson and J. R. Hinthorne in *Earth and Planetary Science Letters* 14, at 195–200 (1972); R. W. Hinton and J. V. P. Long in *Earth and Planetary Science Letters* 45, at 309–325 (1979); and W. S. Meddaugh, H. D. Holland and N. Shimuzu in *Ore Genesis, The State of the Art*, edited by G. C. Amstutz et al (Springer-Verlag 1982). The signal/background advantage is often lost in a slough of molecular ion peaks (metal oxides, hydrides and hydroxides) which are part of the mass spectrum. (FIG. 2) This is an acute problem in geological specimens which typically contain a large number of elements at both major and trace levels. These samples are commonly insulators, or semiconductors at best, and surface charging has introduced further limitations in using the ion beam for analysis. Charging can result in distortion and instability of the primary beam, and is typically minimized using a negatively charged primary beam, conductive coatings (as set out A. Lodding, S. J. Larsson and H. Odelins in *Z. Naturforsch* 339 at 697–708 (1978)), low primary beam currents (as set out by M. G. Dowsett, R. M. King and E. H. C. Parker in *Surface Science* 71 at 541–547 (1978)), or by placing metal grids over the specimen surface (as set out by G. S. Slodzian in *Ann. Phys.* 9 at 591 (1964)). Werner and Morgan in *J. Appl. Phys.* 47, 1232–1242 (1976) proposed that a small conductive aperture set above the insulating specimen surface could confine and stabilize charging. Experimental proof of this concept has been provided by our recent studies.

Two methods have been developed to reduce the molecular interference problem. If very high mass resolution can be obtained, as in the CAMECA instrument, molecular ions such as $^{40}Ca^{16}O^+$ can be distinguished from $^{56}Fe^+$ on the basis of mass defects. However, the resulting intensity loss is so large that this method cannot be generally used. A more generally applicable approach has been the use of "kinetic energy analysis" (KEA) of the secondary ions to suppress molecular species. The kinetic energy distributions of atomic and molecular ions usually differ significantly within the lowest 100 eV of energy distribution (FIG. 3), with the molecular ions decreasing in intensity relative to atomic ions at higher kinetic energies. Thus by biasing the sample to $+4400$ V (instead of $+4500$ V) and employing a narrow energy window, the molecular ion/atomic ion contribution can be often decreased considerably. In FIG. 4($a$), the $CrO^+/Cr^+$ ratio is $1\times10^{-3}$, whereas it is close to 1 in a normal spectrum. However, this kinetic energy selection procedure also decreases intensities by 1–2 orders of magnitude, and the molecular ion peaks are often still too large for trace element analysis; in FIG. 2, for example, the complete rare earth elements cannot be analyzed.

Thus, even with the present CAMECA instrument, which is the best one marketed in the world at the present time, complete analysis of complex solids (metals, alloys, semiconductors, minerals, glasses, plastics) cannot be performed. This has necessitated the development of much more expensive instruments such as that of the Isotrace project at the University of Toronto where a multi-million dollar accelerator is used to break up molecular ions.

A number of patents have been addressed to improving the effectiveness of spectrum analysis:

Canadian Pat. No. 995,825 to Brongersma is addressed to an ion scattering spectrometer for analyzing the surface layer of a material, wherein the device has means to produce a primary, substantially mono-energetic ion beam, deflection means to direct a primary ion beam onto the surface layer of the sample, a diaphragm aperture to pass the ions which are scattered at a predetermined angle relative to the axis of the primary ion beam at the surface layer, and an electrostatic analyzer and ion detector to determine the kinetic energy of the scattered ions passing through this diaphragm. The primary ion beam is deflected along the axis of the analyzer via apertures in two coaxial cylindrical electrodes. The diaphragm aperture is substantially annular and coaxial with the analyzer and is positioned to pass ions which are scattered over an angle exceeding 90°.

Canadian Pat. No. 1,015,467 to Brongersma and Walinga discloses an ion scattering spectrometer somewhat similar to the aforementioned device but having the ability to perform structure analysis as well as mass analysis of the surface layer. The device has means for generating a primary substantially mono-energetic ion beam, a diaphragm aperture for passing a secondary ion beam to be analyzed, and an electrostatic analyzer having a detector for determining the kinetic energy of the ions of the secondary ion beam. The electrostatic analyzer comprises two substantially cylindrical coaxial electrode, and the diaphragm aperture is substantially annular and coaxial with the analyzer. The detector comprises a large number of individual detector elements arranged in a ring which is substantially coaxial with the analyzer.

Canadian Pat. No. 996,685 to Van Nieuwland et al. discloses an ion scattering spectrometer wherein there are provided means to produce a primary substantially monoenergetic ion beam, a diaphragm aperture for passing ions which are scattered at the surface layer at a previously determined angle with respect to the axis of the primary ion beam, and an electrostatic analyzer and a detector to determine the kinetic energy of the scattered ions passed through the diaphragm. The detector is annular and the primary ion beam is directed through the aperture in the centre of the detector.

Canadian Pat. No. 1,021,882 to Erickson and Smith discloses an ion scattering spectrometer utilizing a charge exchange process, wherein the composition of a surface is determined by measuring the loss of kinetic energy as a result of binary scattering.

Canadian Pat. No. 1,048,163 to Le Gressus et al discloses a process of an apparatus for elementary and chemical analysis of the energy of secondary electrons emitted by the sample when the sample is exposed to a monoenergetic beam of primary electrons concentrated on the surface of the sample (i.e., the examination of a sample by the spectrum of Auger emission). The intensity of a beam of monoenergetic primary electrons emitted by an electron gun is modulated according to a sinusoidal law. The secondary electrons emitted by the sample are collected and the intensity of the collected beam is detected.

Canadian Pat. No. 943,670 to Goff discloses an ion scattering spectrometer capable of the surface analysis of insulating materials. Ion generating means produce a monoenergetic beam of primary ions and an energy analyzer receives primary ions scattered from the surface of the target and transmits ions having a preselected kinetic energy value to ion detector means. The ion surface analyzer incorporates a device for neutralizing the accumulative charging of the target so as to permit elemental surface analysis of electrically non-conductive specimens.

Canadian Pat. No. 1,058,772 to McKinney and Goff discloses an ion scattering spectrometer with two independent analyzers positioned adjacent to the material surface for determining the mass and kinetic parameters of ions scattered from the surface. By predetermining conditions within the analyzers so that only ions having certain and different characteristics can pass through each analyzer, a signal characteristic of surface atoms having a given mass can be generated.

Canadian Pat. No. 1,023,061 to Valentine and Goff discloses an improved technique for compositional depth profile analysis applicable to Ion Scattering Spectroscopy and Secondary Ion Mass Spectroscopy. A primary ion beam is caused to traverse and to impinge on a predetermined region of the sample surface, whereupon atoms on the surface within that region are sputtered from the surface. Ions, indicative of the surface region, as have a given mass are transmitted and detected.

Canadian Pat. No. 1,118,913 to Colby and Hull discloses a method of and apparatus for elemental analysis of solids by mass spectrometry, wherein the initial kinetic energy spread of the ions from the solid sample is relatively low, permitting simplification of the mass analyzer which need no longer be of the energy focussing type.

These patents have been presented herein only as background for the present invention.

DETAILED DESCRIPTION OF THE INVENTION

Figure 5:
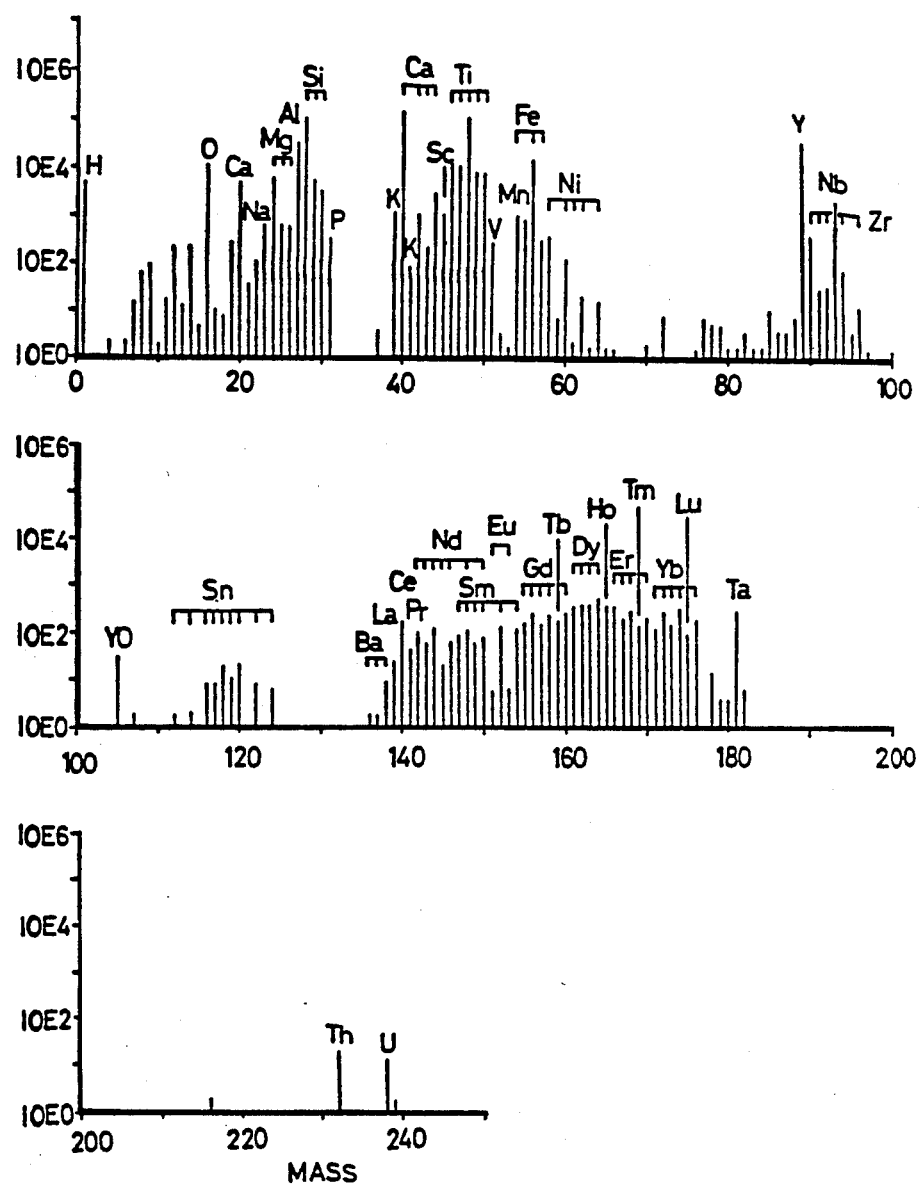
FIG. 5: The mass spectrum of an yttrotitanite specimen under SI conditions.
Figure 6:
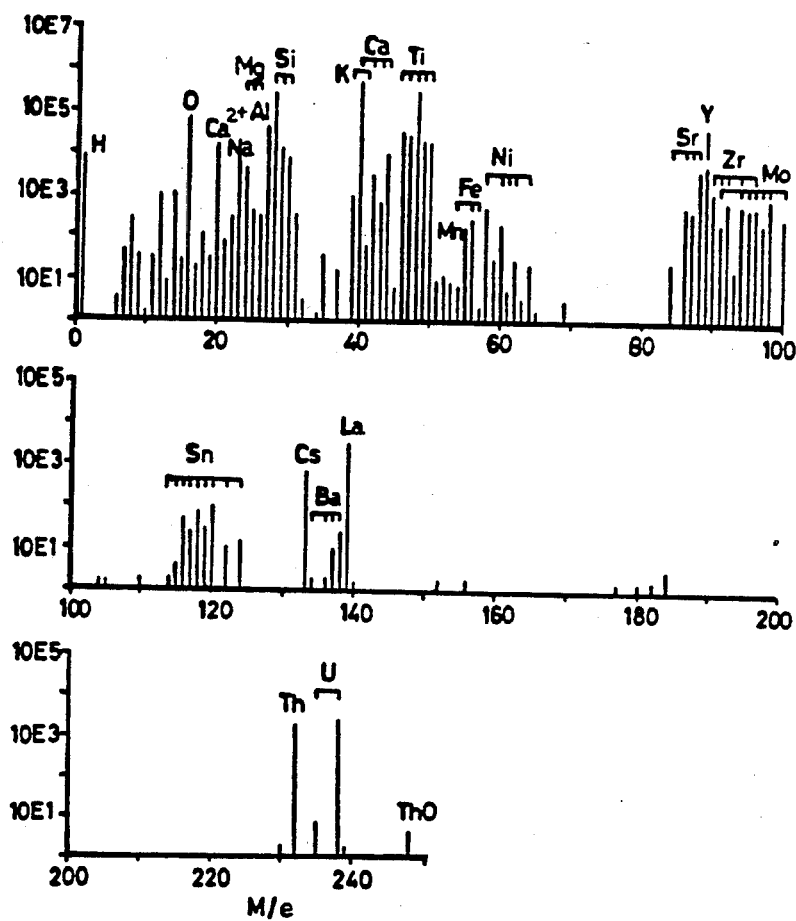
FIG. 6: The mass spectrum of an uncoated sphene ceramic under SI conditions - compare with FIG. 2.

Charging a sample by means of the primary ion beam or by means of an externally attached power source, such that the potential difference between the sample surface and the mask of the sample holder is in excess of 300 V, with a specimen aperture of the proper size, produces two unexpected effects. First, the molecular ion intensities are decreased much more than in ordinary KEA. Thus, in FIG. 4(b), the $CrO^{30}/Cr^+$ is $6 \times 10^{-6}$ compared to $1 \times 10^{-3}$ in FIG. 4a. Second, the intensity obtained is considerably higher than in ordinary KEA. In FIG. 4(b), the $Fe^+$ intensity is about an order of magnitude higher than in FIG. 4(a). Complete analysis of all the elements of interest is now possible and the potential of the SIMS technique can now be fully realized. Other spectra of minerals taken under the present conditions are shown in FIGS. 5 and 6; these can be compared with the spectra, taken under normal conditions, depicted in FIG. 2. Note that in the latter Figures all the significant peaks have been assigned, and there are no molecular ions above ten counts.

Figure 2:
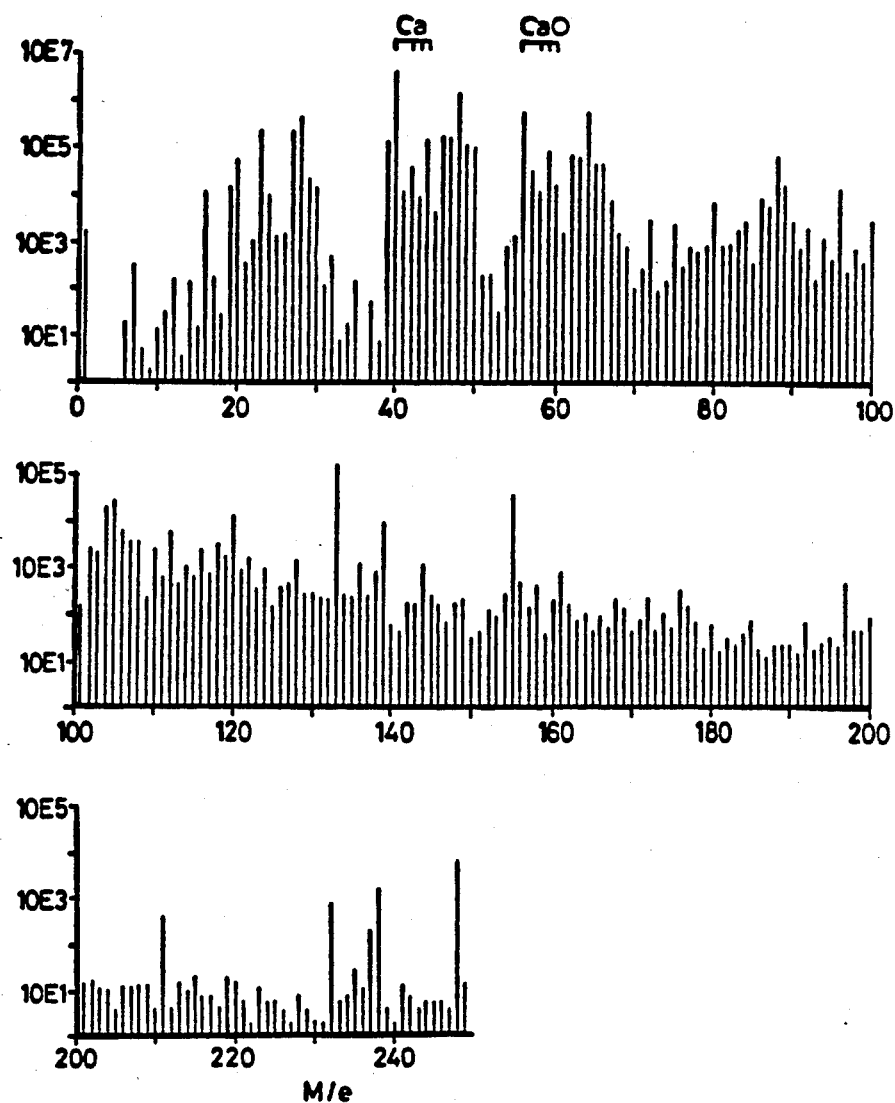
FIG. 2: Mass spectrum of a gold coated sphene ($CaTiSiO_5$) ceramic under normal machine conditions.

Note that this effect is unexpected because the normal kinetic energy curves depicted in FIG. 2 suggest that charging to higher voltages (to look at higher energy ions) would lead to a further decrease in intensity. The reason that this does not happen is mainly due to a focussing lens effect between the floating sample surface and sample holder, and the use of a wide energy window.

This new approach to the suppression of molecular ions in secondary ion mass spectra makes use of a commercially available magnetic sector secondary ion microscope/mass analyzer, such as the CAMECA IMS 3f instrument described by G. Slodzian in *NBS Spec. Publ.* 427 (1975). This instrument uses a duoplasmatron or other primary ion source and either $O_2^+$, $O^-$, $Cs^+$ or $Ar^+$ primary ion beams. A primary ion beam mass filter can be put in place. Generally, a primary beam current of 100–200 nA of $O^-$ or 500–1000 nA of $Cs^+$ is focussed into a 50 μm spot and can, if desired, by rastered over a $250 \times 250$ μm area.

Figure 1:
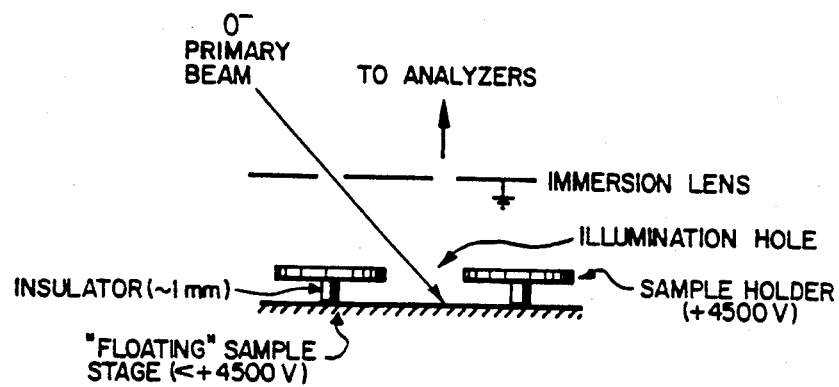
FIG. 1: Experimental arrangement of the specimen holder for secondary Ion Mass Spectrometry by the Specimen Isolated (SI) method in the Cameca IMS 3f.

The only modifications to the normal instrumentation occurs in the specimen holder. The specimen, normally mounted in contact with the stage, is instead isolated electrically and offset behind the stage with a 1 mm TEFLON (TM) spacer. (FIG. 1) A tantalum mask with a 3–5 mm diameter hole is secured above the specimen and attached electrically to the stage. The specimen potential can be allowed to float freely, controlled by the primary and secondary ion currents in equilibrium, or the specimen or specimen and mask potentials can be controlled by a high voltage power supply. The basis of our technique is thus the existence of a potential difference between the sample surface and the mask of the sample holder. This potential difference can be externally supplied (by a power supply attached to the sample) or internally (by the primary ion beam).

Figure 7:
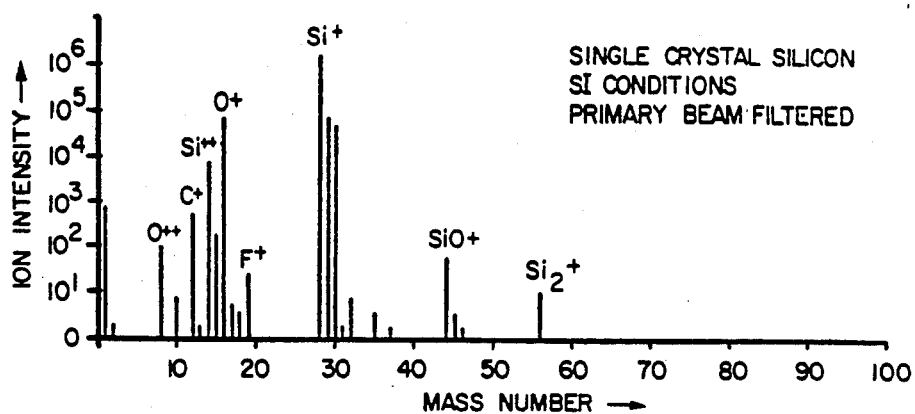
FIG. 7: The mass spectrum of a silicon single crystal obtained using the SI conditions.

Initial experiments disclosed that evidence of molecular ions in the spectrum was reduced dramatically when an electrically insulated specimen surface was bombarded with a diffuse beam of O- ions. This molecular ion suppression effect was applied to the analysis of semiconductors such as silicon, conductors such as metals, and insulators such as minerals with the following results:

(i) Silicon - A specimen of polished single crystal silicon was mounted in the spectrometer, so that it was electrically isolated from the mask. A mass filtered $O^-$ primary beam produced the positive secondary ion spectrum shown in FIG. 7.

A normally mounted specimen of silicon would contain large contributions from moleculars such as $SiO^+$, $Si_2^+$, $Si_2O^+$, etc. with typical $SiO^+/Si^+$ intensity ratios of $\sim 5 \times 10^{-2}$. In this case, using the specimen isolation (SI) technique, the only molecular ions visible, within a factor of $10^{-6}$ of $Si^+$, are $SiO^+$ and $Si_2^+$. Thus, contributions from surface impurities such as $Fe^+$, $Ni^+$, $Cu^+$, $Zn^+$ and $Sb^+$ become more readily detectable. Of particular interest, is the very low contribution from $^{30}SiH^+$ at mass 31, which normally masks the detection of phosphorus.

Figure 4A:
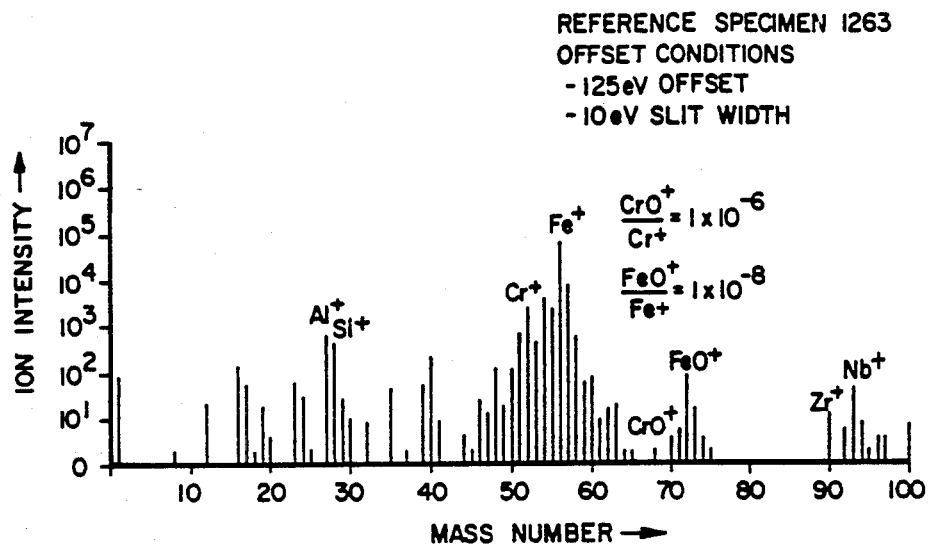
FIGS. 4A-4B: A comparison of SIMS spectra of NBS reference material 1263 under SI conditions and normal Cameca voltage offset conditions both with an $O^-$ primary beam.
Figure 4B:
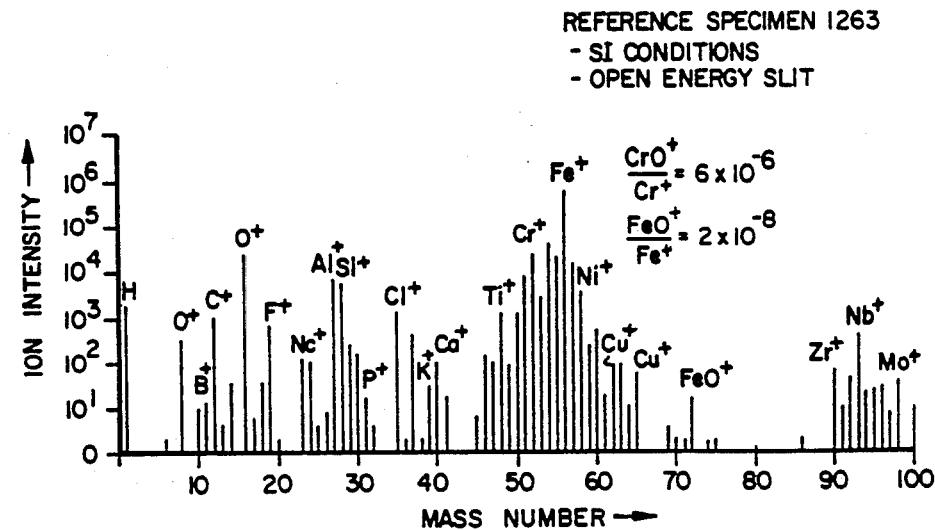

(ii) Steel Alloy Reference Material - a series of NBS 1260 series iron alloys were analyzed, both under electrically isolated (SI) conditions (FIG. 4b) with an external voltage controlling the specimen potential, and under normal CAMECA offset conditions (FIG. 4a).

The molecular ion suppression increased with the potential difference applied between the specimen surface and the normal mask voltage (+4500 V). Total secondary ion current decreased with the potential difference. The spectrum obtained with a potential difference of $-300$ volts is shown in FIG. 4b.

Molecular ions such as $FeO^+$ and $CrO^+$ are about 3-4 orders of magnitude lower in intensity than they would be in an equivalent spectrum taken under nonisolated conditions. As a result, minor and trace elements, particularly those with $M/e > 60$, are more readily detectable.

Linear calibration plots for the alloy series yield the following (3) detection limits in an iron matrix: Ti-0.6 ug/g; Cr-2 ug/g; Cu-15ug/g and As-70 ug/g.

Previously used methods of kinetic energy analysis in SIMS (set out by N. Shimizu in *Nature* 289 at 575 (1981)) have also produced appreciable suppression of the molecular ion component, but not to the same extent as in these present experiments. In the CAMECA IMS-3f the normal method of kinetic energy analysis is to offset the normal specimen stage bias by up to 125 volts and to reduce the kinetic energy spread passed through the electrostatic analyzer to 10 eV. The use of such a procedure with the same alloy standard is shown in FIG. 4a. Both offset voltage and slit widths were set to obtain a minimum $FeO^+/Fe^+$ ratio. The suppression factor obtained was about two orders of magnitude less than obtained by specimen isolation (FIG. 4b) and was achieved with an overall loss in ion intensity.

Figure 8A:
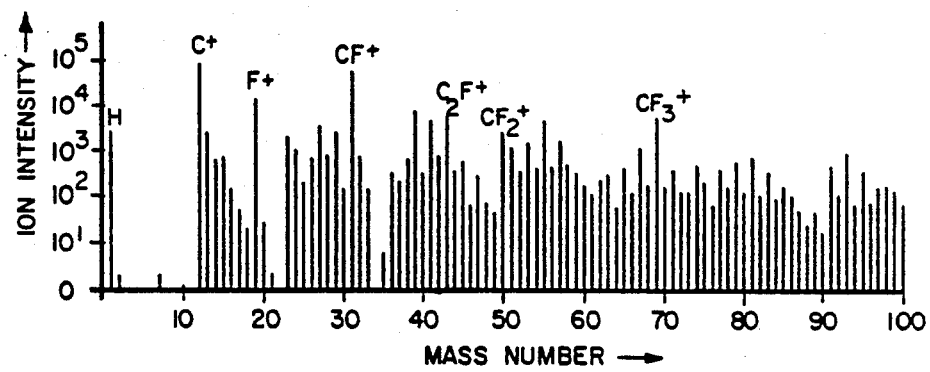
FIGS. 8A-8B: Mass spectra of a TEFLON (TM) sample under
(a) normal no offset conditions and
(b) SI conditions.
Figure 8B:
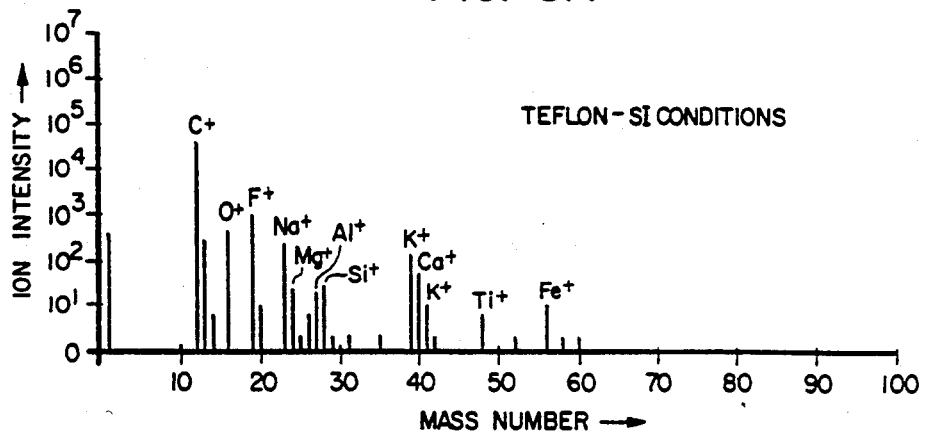

(iii) Polymers - The spectrum of a TEFLON sample under our SI conditions (FIG. 8b) shows the almost total absence of all the molecular ions present in a normal spectrum (FIG. 8a). Trace metal contaminants can now be readily analyzed using our approach.

(iv) Geologic Specimens: The analysis of ceramic and mineral surfaces has been very desirable for the study of isotope ratios, surface transformations and trace element microdistribution. However, the spectra are usually rather complex due to molecular ion contributions, and charging of the surface often reduces or completely eliminates the secondary ion current. The use of specimen isolation conditions for the analysis of minerals has thus been particularly valuable. Insulating specimens are sometimes mounted with a sputtered gold overlayer, but our specimens have been successfully analyzed with no overlayer, since the geometric arrangements appears to create conditions leading to a stable charge equilibrium, not usually encountered with insulators in SIMS experiments.

Figure 9:
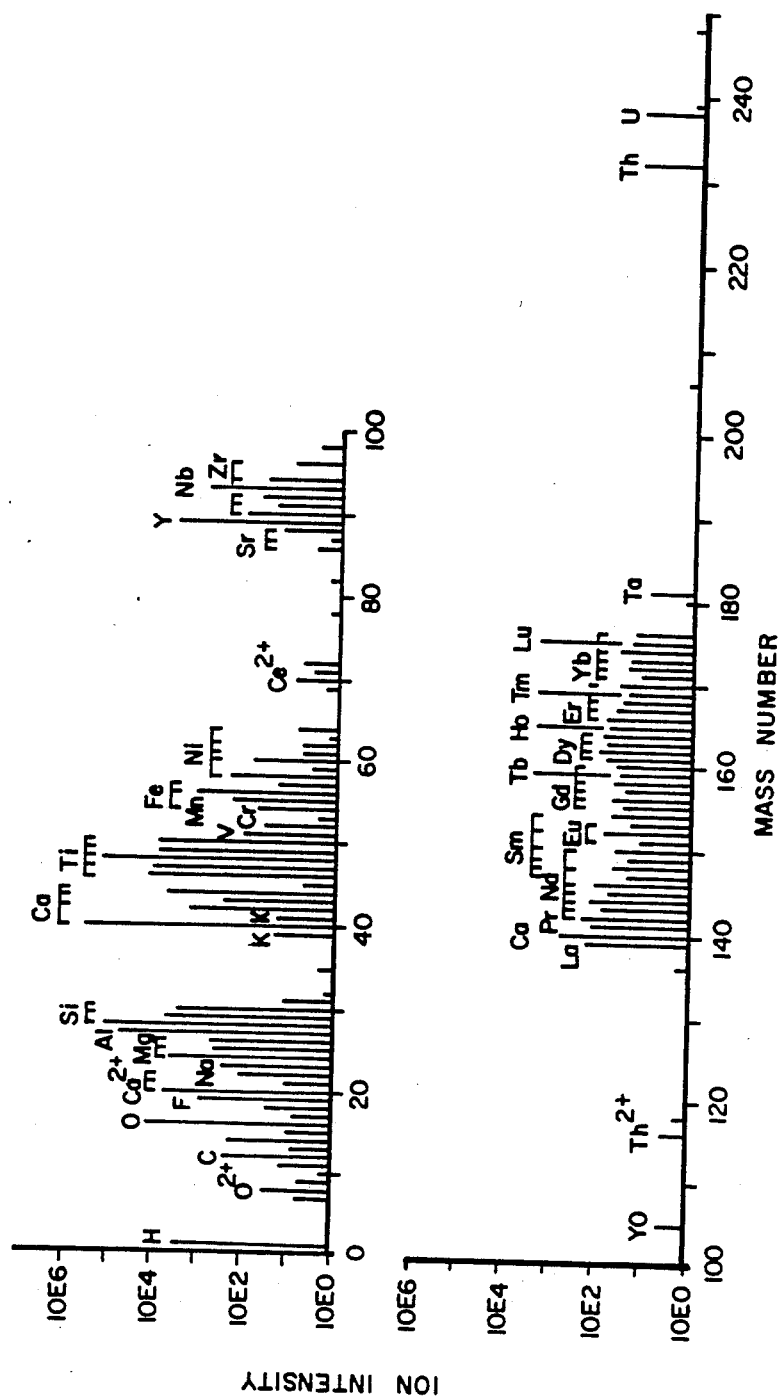
FIG. 9: The mass spectrum of a natural sphene from Cardiff Mine Ontario.

A SIMS spectrum of a natural sphene ($CaSiTiO_5$) mineral, with an uncoated surface is shown in FIG. 9. Of particular note is the almost total absence of visible oxide peaks and the clear indications of the trace lanthanide and actinide elements.

In another series of experiments, specimens analyzed included a sphene from Gjerstad, Norway (M28173), a yttrium and cerium rich sphene (yttrotitanite) from Arendal, Norway (EV502) a uraninite from Cardiff Mine, Ontario and zircons and hornblendes, also from Ontario.

Samples used for analysis were mineral fragments of 5–20 mm diameter, lightly polished on a 30 μm diamond impregnated wheel and mounted directly, uncoated in the specimen holder. The sample was supported against a thin tantalum sheet with ≈3 mm holes through which the specimen surface was exposed. The sample holder was then maintained at 4.5 keV relative to the immersion lens to accelerate positively charged ions into the secondary column. Lens settings in the primary column were optimized for maximum secondary ion yield; this maximum yield consistently occurred with the first primary lens ($L_1$) adjusted beyond the point where maximum beam current is detected at the faraday cup.

Using this method, conditions in the secondary column (i.e. contrast aperture, field aperture and final kinetic energy selection) made considerably less difference to the mass spectrum, than does the conductivity of the sample itself. Insulating specimens were usually examined with all apertures in the secondary column fully open. With semiconductors such as uraninite it was necessary to use the TEFLON (TM) insulation between the specimen and the tantalum mask.

Figure 10:
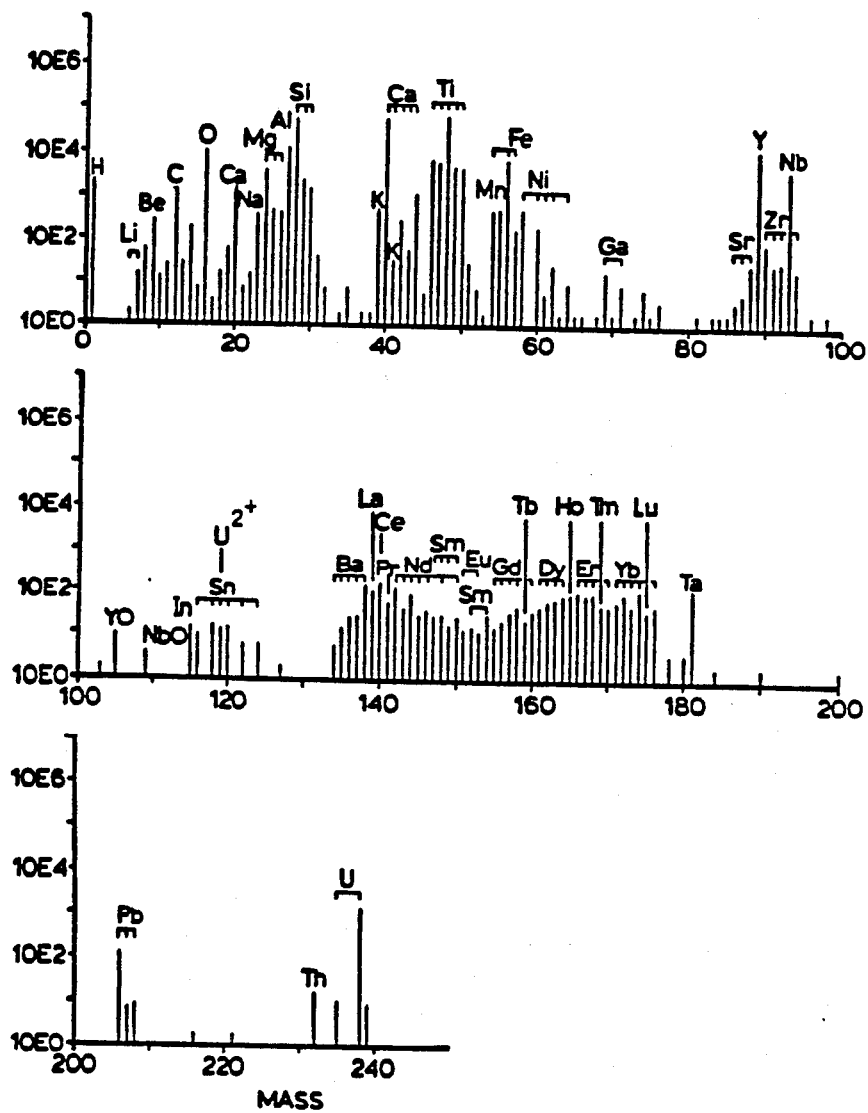
FIG. 10: The mass spectrum of a natural sphene from Gjerstad, Norway.

Results obtained were as follows:

Mass spectra of a natural sphene and a yttrotitanite are shown in FIGS. 10 and 5 respectively. The two specimens have similar compositions apart from Y and Ce levels. Both spectra clearly show all the rare earth elements, thorium, uranium and radiogenic Pb. The absence of a peak at M/e=204 confirms the absence of common lead in both samples.

The spectra are virtually free of interferences from molecular ions through the entire mass range examined (M/e=1→250). The yttrotitanite spectrum was analysed in detail to obtain isotope ratios of a number of major, minor and trace elements (see Table 1). The fact that the observed ratios for Fe agree with literature values is very encouraging, as interferences in this area of the spectrum are usually a major problem. The iron peak at M/e=54 can contain a component from $Al_2^+$, while M/e=56 is subject to interferences from $Si_2^+$ and $CaO^+$, two of the most likely molecular ions in the spectrum. M/e=57 is similarly affected by $Si_2H^+$ and $CaOH^+$. The excellent agreement with theoretical values for the three isotopes examined indicates very little interference from molecular ions in the spectrum. This is also true of the five Ti isotopes, which show good agreement with literature values.

The isotope ratios of the elements Sm, Gd and Yb in Table 1 are in excellent agreement with literature values. The observed ratios indicate there is virtually no interference from hydrides and no measurable contamination of the heavy rare earth peaks from oxides of the light RE's. Accurate determinations of relative rare earth levels are possible with this method, offering far greater ease than the neutron activation methods currently employed.

Measurement of the relative intensities of $^{48}Ti^+$ and $^{64}(TiO)^+$ serves as a useful guide to the extend of all molecular ion discrimination. In the yttrotitanite spectrum (FIG. 15) the $^{48}Ti^+/^{64}(TiO)^+$ exceeds $10^4/1$, afer the correction for a contribution by $^{64}Ni^+$. By contrast, using an $O2/+$ primary beam and gold coating the specimen to reduce charging, a $^{48}Ti^+/^{64}(TiO)^+$ ratio of 1–10 usually results.

Figure 11:
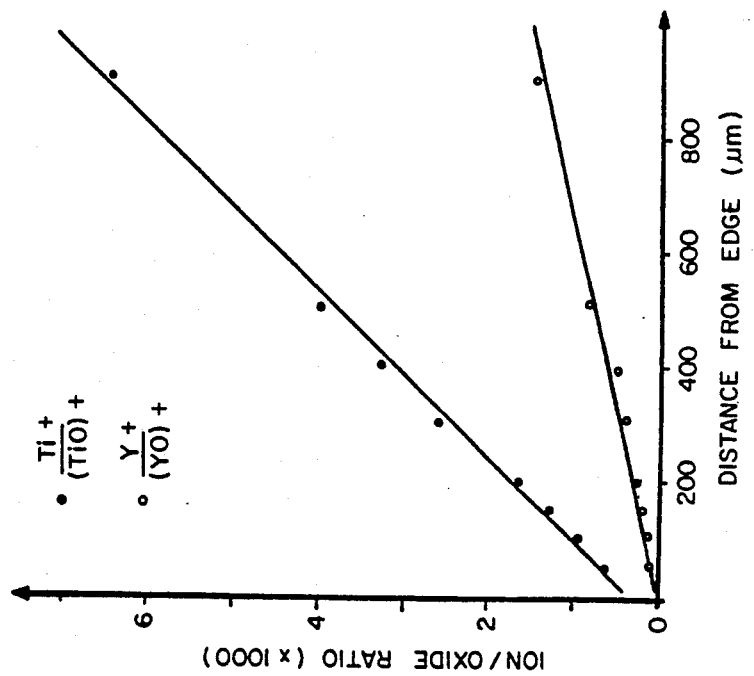
FIG. 11: The increase in $Ti^+/TiO^+$ and $Y^+/YO^+$ as a function of distance between the analysis point on the specimen and the edge of the aperture of the specimen holder, for a yttrotitanite specimen.

The suppression of molecular ions has been found to be a function of the distance between the analysis point on the specimen and the edge of the electrically conducting specimen holder. FIG. 11 shows the increase in $^{48}Ti^+/^{64}(TiO)^+$ and $^{89}Y^+/^{105}(YO)^+$ as a function of this distance for the yttrotitanite specimen. The increase in molecular ion suppression is accompanied by a loss in intensity of all secondary ions. The intensity of $^{48}Ti^+$ drops 50 fold between an analysis point at the sample edge and a point 1200 μm away from that edge (see FIG. 12). The ratios of atomic ions from different elements do not appear to be affected by the position of the primary beam except within 200 μm of the aperture edge.

Figure 3:
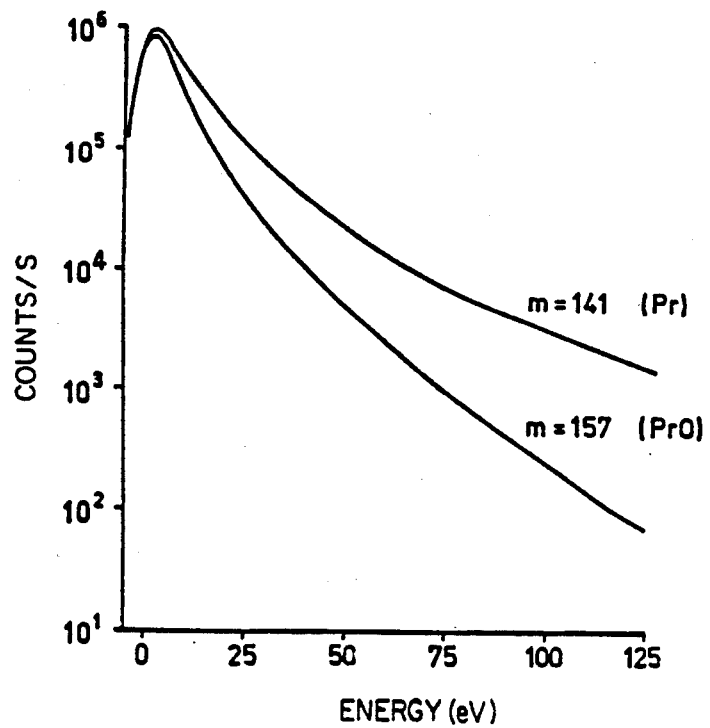
FIG. 3: The kinetic energy distributions of an elemental ion ($Pr^+$) and its molecular ion oxide ($PrO^+$).
Figure 13:
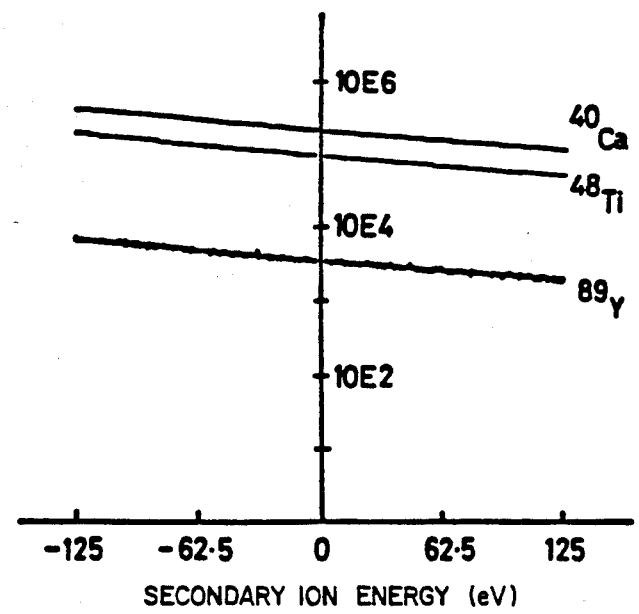
FIG. 13: The energy distribution of ions as a function of machine applied voltage offset on the sample holder mask under SI conditions from a yttrotitanite specimen.

FIG. 13 shows energy distributions using the machine offset facility in the SI mode. The straight lines indicate that the mass spectrum is being obtained well out on the high energy tail of the elemental ion energy distribution in contrast with FIG. 3.

Although our understanding of the molecular ion suppression effect is still not complete, it appears that some of the effects result from an extreme discrimination on the basis of difference in the kinetic energies of atomic and molecular ions. It is also clear that for nonconducting specimens, the effect is not achieved simply by a larger energy filtering than is normally used in the CAMECA IMS-3f. It has been assumed in the past that kinetic energy selection by offset voltage requires a concommittant decrease in energy selector band pass with a resultant severe loss of intensity. It appears that much better suppression factors result from a larger kinetic energy offset (400–500 eV) with no decrease in band pass. The ion intensity available for analysis at kinetic energies of 400 eV is surprisingly large. The present specimen isolation mount creates a focussing effect above the specimen surface.

Figure 12:
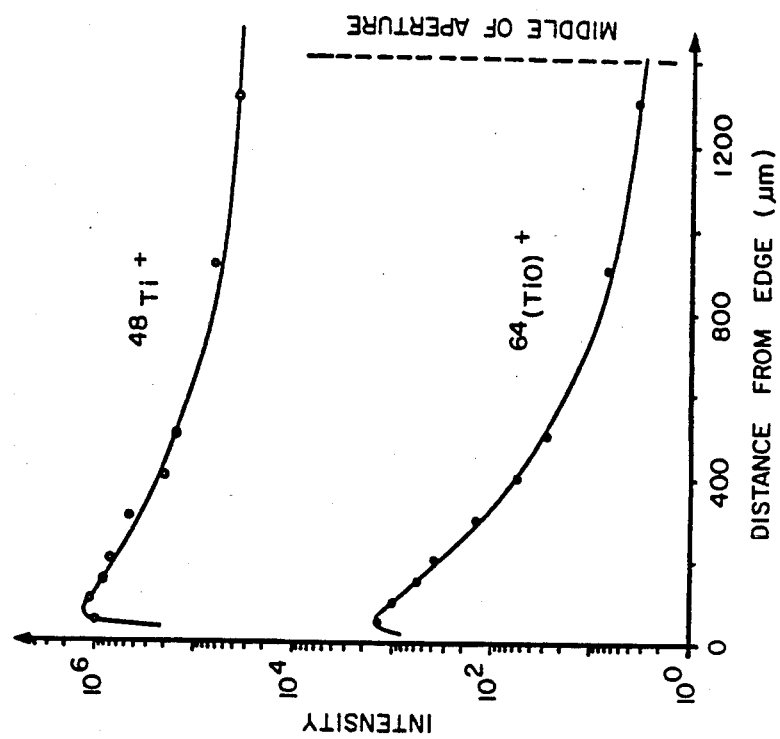
FIG. 12: The loss of intensity for both elemental ions and molecular ions as a function of position in the specimen holder aperture for the yttrotitanite specimen.

The curve shown in FIG. 12 is qualitatively similar to a plot of secondary ion intensity as a function of kinetic energy. This suggests that moving the primary beam away from the sample holder edge simply allows greater surface charging and effectively causes an offset in the secondary accelerating voltage. Thus most of the discrimination we observe can be attributed to an extreme kinetic energy selection. By allowing the surface to charge, the voltage offset obtained causes selection of only high energy (elemental) ions. The major advantages of this approach are that the molecular ions are suppressed more than in the usual kinetic energy selection and that the intensity loss suffered in obtaining high levels of discrimination is not as prohibitive as the use of a narrow kinetic energy window.

Experiments with an applied voltage on a conducting sample suggest that the insulating surface must be reaching potentials of at least 3–4 hundred volts (~4.2 keV) during ion bombardment. At these potentials, a near linear portion of the kinetic energy curve has been reached and the molecular ions are strongly suppressed. The large offset and spread in kinetic energies is so broad that no energy analysis is required in the secondary column.

The ion beam conditions necessary to maintain a charging but stable surface are apparently critical. An ion beam focussed to a small (1→5 μm) spot, produces few or no secondary ions from an insulating, uncoated surface. Apparently, the use of an overfocussed beam may delocalize charge on the surface. The stabilization of surface charging on insulators is an important side-benefit of this method.

The aforementioned experiments indicate that secondary ion mass spectra virtually free of molecular ions have been obtained for all classes of solid samples. Intensities obtained are quite adequate for the rapid analysis and detection of most trace elements. The critical parameter is obtaining these spectra appears to be the controlled charging of the specimen surface. An equilibrium condition between the negative primary oxygen beam and the area being bombarded is established rapidly on uncoated specimens, as evidenced by the excellent stability of the secondary ion signals from these materials.

TABLE 1

Observed and Natural Abundances of the Isotopes of five elements in sample EV502

| Element | Ti | | | Fe | | | Sm | | | Gd | | | Yb | | |
|---|---|---|---|---|---|---|---|---|---|---|---|---|---|---|---|
| Isotope | Mass | Obs. | Nat. Ab. | Mass | Obs. | Nat. Ab. | Mass | Obs. | Nat. Ab. | Mass | Obs. | Nat. Ab. | Mass | Obs. | Nat. Ab. |
| | 46+ | 8.54 | 7.93 | 54 | 6.02 | 5.82 | 144* | | 3.09 | 154* | | 2.15 | 170* | | 3.03 |
| | 47 | 7.64 | 7.28 | 56 | 91.8 | 91.66 | 147 | 15.4 | 15.0 | 155 | 14.0 | 14.7 | 171 | 14.7 | 14.3 |
| | 48+ | 72.94 | 73.94 | 57 | 2.02 | 2.19 | 148* | | 11.2 | 156 | 20.7 | 20.5 | 172 | 22.3 | 21.8 |
| | 49 | 5.56 | 5.51 | 58* | | 0.33 | 149 | 13.1 | 13.8 | 157 | 16.2 | 15.7 | 173 | 14.8 | 16.1 |
| | 50 | 5.32 | 5.34 | | | | 150* | | 7.44 | 158 | 24.8 | 24.9 | 174 | 31.9 | 31.8 |
| | | | | | | | 152 | 26.4 | 26.7 | 160* | | 21.9 | 176* | | 12.7 |
| | | | | | | | 154* | | 22.7 | | | | | | |

+Peak intensities were corrected for calcium isotope contributions.
*These isotopes were masked by isotopes of other elements.

I claim:

1. A method of suppressing molecular ions in the secondary ion mass spectra of a solid specimen of insulating or semiconducting material and removing charge distortions from the spectra of insulating materials, said method comprising the steps of:
   mounting said specimen of insulating or semiconducting material uncoated in a specimen holder such that said specimen is isolated electrically and offset behind the stage of a secondary ion microscope/mass analyzer;
   securing a mask above said specimen, said mask being attached electrically to said stage;
   impinging on said speciment a high energy primary ion beam to produce secondary ions;
   charging said specimen such that a potential difference in excess of 300 V exists between the surface of said specimen and said mask;
   focussing said secondary ions through an immersion lens into an analyzer;
   recording the secondary ion mass spectra of said specimen.

2. The method of claim 1, wherein said primary ion beam supplies said potential difference between said specimen surface and said mask of said specimen holder.

3. The method of claim 1, wherein a high voltage power supply attached to said specimen supplies said potential difference between said specimen surface and said mask of said specimen holder.

4. The method of claim 1, wherein said high energy primary ion beam is a negatively charged monatomic ion beam.

5. The method of claim 4, wherein said negatively charged monatomic ion beam is comprised of $O^-$ ions.

6. The method of claim 1, wherein said high energy primary ion beam is a positively charged monatomic ion beam.

7. The method of claim 6, wherein said positively charged monatomic ion beam is comprised of $Ar^+$ ions.

8. The method of claim 1, wherein said high energy primary ion beam is a positively charged ion beam and wherein said positively charged ion beam is comprised of $O_2^+$ ions.

9. The method of claim 6, wherein said positively charged ion beam is comprised of $Cs^+$ ions.

10. The method of claim 1, 10 or 11, wherein said specimen holder is maintained at 4.5 keV relative to said immersion lens.

11. The method of claim 1, wherein said solid specimen is a silicon semiconductor.

12. The method of claim 1, wherein said solid specimen is an insulator selected from the group consisting of a mineral, glass or plastic.

13. The method of claim 1, wherein said uncoated specimen of insulating or semiconducting material in said specimen holder is supported against a thin tantalum sheet through which said specimen surface is exposed to said high energy primary ion beam.

14. The method of claim 4, wherein said uncoated specimen of insulating or semiconducting material in said specimen holder is supported against a thin tantalum sheet through which said specimen surface is exposed to said high energy primary ion beam.

* * * * *